United States Patent [19]

Schimmel et al.

[11] 4,410,466

[45] Oct. 18, 1983

[54] PROCESS FOR EXTRACTIVELY SEPARATING A MIXTURE CONTAINING PHOSPHORIC ACID MONOALKYLESTERS INTO ITS COMPONENTS

[75] Inventors: Günther R. Schimmel; Werner Klose, both of Erftstadt, Fed. Rep. of Germany

[73] Assignee: Hoechst Aktiengesellschaft, Fed. Rep. of Germany

[21] Appl. No.: 327,429

[22] Filed: Dec. 4, 1981

[30] Foreign Application Priority Data

Dec. 11, 1980 [DE] Fed. Rep. of Germany ....... 3046631

[51] Int. Cl.$^3$ .............................................. C07F 9/09
[52] U.S. Cl. .................................. 260/990; 260/963
[58] Field of Search ........................................ 260/990

[56] References Cited

PUBLICATIONS

Stewart et al., "Jou. Am. Chem. Soci." vol. 73, (1951) 1377-1378.
Kosolapoff et al. "Organic Phosphorus Compounds," vol. 6, (1973), pp. 229-230.

*Primary Examiner*—Anton H. Sutto
*Attorney, Agent, or Firm*—Connolly and Hutz

[57] ABSTRACT

The invention relates to a process for separating a mixture containing phosphoric acid monoalkylesters, phosphoric acid dialkylesters and minor proportions of diphosphoric acid dialkylesters, each with 6 to 12 carbon atoms in the alkyl radical, by extractively distributing them between an aliphatic or aromatic hydrocarbon as an unpolar solvent and a polar solvent. To this end, the invention provides: for the ester mixture to be admixed with the quantity of water stoichiometrically necessary for hydrolyzing the P-O-P-bond of the diphosphoric acid dialkylester with the resultant formation of the phosphoric acid monoalkylester; for the whole to be maintained for at least 1 hour at temperatures higher than 60° C.; for the partially hydrolyzed ester mixture to be treated in a countercurrent apparatus comprising n-stages with the solvents immiscible or partially miscible with one another so as to ensure introduction of pure solvent into stage 1 and stage n, respectively, and the introduction of partially hydrolyzed mixture into one of the stages 2 to (n−1), n standing for a whole number of at least 3.

9 Claims, No Drawings

PROCESS FOR EXTRACTIVELY SEPARATING A MIXTURE CONTAINING PHOSPHORIC ACID MONOALKYLESTERS INTO ITS COMPONENTS

The present invention relates to a process for separating a mixture of phosphoric acid esters into its components, the mixture being obtained, for example, by reacting an aliphatic $C_6$ to $C_{12}$-alcohol with phosphorus pentoxide ($P_4O_{10}$). Depending on the stoichiometric ratio selected for the starting materials and the reaction conditions, the mixture may contain, for example, from 30 to 60 weight % of phosphoric acid monoalkylesters and phosphoric acid dialkylesters, respectively, together with 2 to 15 weight % diphosphoric acid dialkylesters.

Mixtures of acid phosphoric acid alkylesters find very widespread uses, e.g. as cleaning components, metal processing liquids and emulsifiers, whereas the pure phosphoric acid mono- or dialkylesters are used, e.g. as selective complexing agents in the extraction of metals. Di-(2-ethylhexyl)-phosphate in the form of an about 10 weight % solution in kerosene has proved particularly useful.

It is an object of this invention to provide a process permitting the above mixture of phosphoric acid alkylesters to be readily separated into its components, and especially the dialkylester to be obtained free from the corresponding monoalkylester.

It has been described that phosphoric acid monoalkylesters and dialkylesters can be separated from each other by reason of their different structure and hydrophilic properties provided that use is made of the different distribution coefficients of the two substances in two solvents being immiscible with one another.

U.S. Pat. No. 2,658,909 describes water-insoluble organic solvents which in combination with water or diethyleneglycol permit the above phosphoric acid alkylester mixture to be partially separated into the phases forming. GB-PS No. 778 081 suggests that monoethyleneglycol in combination with a cycloaliphatic or aromatic hydrocarbon should preferably be used as the pair of solvents for separating the various phosphoric acid alkylester components from each other.

Needless to say, a one-step extraction permits the various components to be separated from each other incompletely only inasmuch as a portion of the component to be separated goes into one and the same phase together with the principal component. To complete the separation, it is therefore necessary for the two extracts to be repeatedly washed, each time with fresh solvent. Diphosphoric acid dialkylesters are known for their selectivity behaviour which is even less pronounced than that of the corresponding orthophosphoric acid alkylesters. It can even be evidenced that the presence of a diphosphoric acid dialkylester hinders the separation of the two other esters into the phases forming (cf. Examples 1 and 2 and 5 and 6).

The present invention relates more particularly to a process for separating a mixure containing phosphoric acid monoalkylesters, phosphoric acid dialkylesters and minor proportions of diphosphoric acid dialkylesters, each with 6 to 12 carbon atoms in alkyl radical, by extractively distributing them between an aliphatic or aromatic hydrocarbon as an unpolar solvent and a polar solvent, which comprises:

(a) admixing the ester mixture with the quantity of water stoichiometrically necessary for hydrolyzing the P-O-P-bond of the diphosphoric acid dialkylester with the resultant formation of the phosphoric acid monoalkylester, allowing the whole to remain for at least 1 hour at temperatures higher than 60° C., and (b) treating the partially hydrolyzed ester mixture in a counter-current apparatus comprising n-stages with the solvents, which are immiscible or partially miscible with one another, so as to ensure introduction of pure solvent into stage 1 and stage n, respectively, and the introduction of partially hydrolyzed ester mixture into one of the stages 2 to (n−1), n standing for a whole number of at least 3.

Further preferred features of the present invention which can be used individually or in combination provide:

(c) for a temperature of 80° to 100° C. to be used in partial step (a) and for the hydrolysis to be effected over a period of 2 to 4 hours;

(d) for n to stand for a whole number of 3 up to 50;

(e) for the untreated ester mixture to contain 30 to 60 weight % each of phosphoric acid mono- and dialkylesters and 2 to 15 weight % of diphosphoric acid dialkylesters;

(f) for 1 to 3 parts by weight polar solvent and 1 to 3 parts by weight unpolar solvent to be used per part by weight partially hydrolyzed ester mixture;

(g) for the partially hydrolyzed ester mixture to be metered into stage n/2 or, in the event of n standing for an uneven number, into stage $n/2+\frac{1}{2}$;

(h) for the polar solvent to be metered into stage 1, for the unpolar solvent to be metered into stage n, and for the partially hydrolyzed ester mixture to be introduced in a stage lying therebetween at a level which is the higher the higher the number of carbon atoms in the alkyl radical and the higher the quantitative ratio of phosphoric acid monoalkylesters to phosphoric acid dialkylesters in the partially hydrolyzed ester mixture;

(i) for the countercurrent apparatus to comprise a mixer/settler unit; and (k) for the countercurrent apparatus to comprise a liquid/liquid extraction column provided with stationary or mobile insert elements.

The useful aliphatic or aromatic hydrocarbons (unpolar solvents) comprise, e.g. petroleum ether (bp=20−60° C.), kerosene (bp=175−325° C.), n-hexane, benzene, toluene, xylene, mesitylene, cyclohexane, tetralene or decalene. Monoethyleneglycol or water should preferably be used as the polar solvent.

Useful liquid/liquid-extraction columns provided with stationary insert elements comprise perforated plate columns and packed columns, and those provided with movable insert elements comprise e.g. columns fitted with liftable plates or agitators.

In the manner described hereinabove, it is possible to ensure an extremely selective and largely quantitative separation of phosphoric acid monoalkylesters and dialkylesters. This is a result of the fact that the P-O-P-bond in the diphosphoric acid dialkylester, which is useless as such, can be hydrolytically split in partial step (a) with the use of water to give 2 molecules of phosphoric acid monoalkylester without the ester linkages undergoing significant hydrolysis.

In those cases in which the extractive separation is effected in n-stages in a liquid/liquid countercurrent extraction apparatus, the mixture to be separated, which is in a solvent, is normally introduced into the 1st stage and the extraction aid is introduced in the $n^{th}$ stage. In carrying out the present process, the separation of the phosphoric acid esters has been found to be considerably more selective and effective if the partially hydrolyzed ester mixture, is not dissolved in one of the extraction aids, but directly metered into the mixer forming part of mean stages provided in the apparatus.

The present process is especially useful for the manufacture of solutions of phosphoric acid dialkylesters in kerosene needed for the extraction of metals. In order to obtain the two esters (mono- and dialkylphosphates) in pure form, the invention provides for the extraction aids, namely ethyleneglycol and hydrocarbon, to be distilled off and circulated.

The following Examples illustrate the separation of various ester mixtures. More particularly, they describe the effect of the hydrolysis of the P-O-P-bond in single step extraction tests, and in the synergistic combination in accordance with this invention of such partial hydrolysis (partial step a) with the countercurrent extraction in accordance with this invention (partial step b).

The analytical data were determined by means of P-nuclear resonance and total P-determination. The R and S values indicated are an index of the quality of separation. R stands for the extraction effectiveness and is defined as follows:

$$R_{mono} = \frac{\text{kg monoester in glycol phase}}{\text{kg monoester used}}$$

$$R_{di} = \frac{\text{kg diester in kerosene phase}}{\text{kg diester used}}$$

S stands for the extraction selectivity and for the purity of the respective phase:

$$S_{mono} = \frac{\text{(kg monoester/kg diester) in glycol}}{\text{(kg monoester/kg diester) used}}$$

$$S_{di} = \frac{\text{(kg diester/kg monoester) in kerosene}}{\text{(kg diester/kg monoester) used}}$$

| Ex. No. | Wgt % of ester components | | | | R | | S | |
|---|---|---|---|---|---|---|---|---|
| | in Kerosene | | in Glycol | | | | | |
| | Mono | Di | Mono | Di | Mono | Di | Mono | Di |
| 1 | 6.0 | 25.6 | 18.8 | 6.3 | 0.75 | 0.81 | 4.0 | 3.2 |
| 2 | 4.9 | 28.0 | 23.3 | 6.7 | 0.83 | 0.81 | 4.3 | 4.7 |
| 3 | 1.0 | 29.0 | 17.5 | 4.0 | 0.97 | 0.79 | 4.6 | 27.5 |
| 4 | 4.9 | 25.7 | 17.5 | 0.9 | 0.80 | 0.96 | 21.4 | 4.8 |
| 5 | 0.6 | 25.5 | 14.6 | 0.6 | 0.97 | 0.97 | 30.0 | 35.2 |
| 6 | 0 | 24.5 | 19.6 | 0.5 | 1.00 | 0.97 | 37.5 | |
| 7 | 0 | 21.5 | 22.3 | 3.5 | 1.00 | 0.88 | 8.1 | |
| 8 | 0.4 | 27.9 | 16.4 | 0.6 | 0.99 | 0.97 | 27.9 | 66.7 |
| 9 | 0.1 | 32.2 | 16.1 | 0.2 | 1.00 | 0.99 | 98.9 | 252.2 |

EXAMPLE 1

(Comparative Example)

Identical quantities of monoethyleneglycol, kerosene (Shellsol T, this is a registered Trade Mark) and ester mixture containing 36.3 weight % mono-(2-ethylhexyl)-phosphoric acid ester, 46.2 weight % di-(2-ethylhexyl)-phosphoric acid ester and 9.3 weight % di-(2-ethylhexyl)-diphosphoric acid ester were intensively stirred for 20 minutes. The whole was allowed to settle and the resulting two phases were analyzed. The separation in the two extracts was incomplete. The kerosene phase contained 2.3 weight % di-(2-ethylhexyl)-diphosphoric acid ester.

EXAMPLE 2

(Comparative Example)

To hydrolyze the P-O-P-bond of the di-(2-ethylhexyl)-diphosphoric acid ester, the ester mixture of Example 1 was admixed with 1.5 weight % water and maintained at 80° C. over a period of 3 hours. Next, the whole was extracted as in Example 1. The separation of the monoester from the diester was considerably better than in Example 1. The kerosene phase could not be found to contan di-(2-ethylhexyl)-diphosphoric acid ester.

EXAMPLE 3

(Comparative Example)

A mixer/settler unit comprising five stages was used and countercurrently passed therethrough per hour was, in stage 1,1000 g monoethyleneglycol and, in stage 5, 1300 g kerosene solution which contained 50 weight % of a phosphoric acid ester mixture (40.8 weight % mono-(2-ethylhexyl)phosphoric acid ester, 46.1 weight % di-(2-ethylhexyl)phosphoric acid ester and 12.0 weight % di-(2-ethylhexyl)-diphosphoric acid ester). Only in the kerosene phase running off could the separation of monoester from diester be found to be satisfactory to some limited extent; it contained 0.7 weight % di-(2-ethylhexyl)-diphosphoric acid ester.

EXAMPLE 4

(Comparative Example)

The procedure described in Example 3 was modified as follows 680 g kerosene per hour was introduced into stage 5 and 1670 g of a glycol solution containing 40 weight % of the ester mixture specified in Example 3 was introduced per hour into stage 1. Only in the glycol phase running off could the separation be found to be satisfactory to some limited extent. About equal parts of the di-(2-ethylhexyl)-diphosphoric acid ester were found to have been distributed on to the two phases.

EXAMPLE 5

(Comparative Example)

A mixer/settler unit comprising 5 stages was used and 900 ml/h monoethyleneglycol was introduced into stage 1 and 900 ml/h kerosene into stage 5. Metered into the mixer of stage 3 was 480 ml/h of a phosphoric acid ester mixture with the composition indicated in Example 1. The separation in two phases was satisfactory; the kerosene phase contained 0.6 weight % di-(2-ethylhexyl)-diphosphoric acid ester.

EXAMPLE 6

(Invention)

The procedure described in Example 5 was modified. To this end, the phosphoric acid ester mixture obtained after the partial hydrolysis described in Example 2 was introduced into stage 3 of the mixer/settler unit. The separation in the two phases was good; the kerosene phase was free from di-(2-ethylhexyl)-diphosphoric acid ester and mono-(2-ethylhexyl)-phosphoric acid ester.

EXAMPLE 7

(Invention)

A phosphoric acid n-hexylester-mixture containing 40.1 weight % monohexylphosphoric acid ester, 50.8 weight % dihexylphosphoric acid ester and 6.1 weight % dihexyldiphosphoric acid ester was treated with 2 weight % water at 80° C. over a period of 3 hours to hydrolyze the P-O-P-bond of the dihexyldiphosphoric acid ester. 500 ml/h of this partially hydrolyzed ester mixture was introduced into the mixer in stage 2 of a mixer-settler unit comprising 5 stages. Conveyed per hour were 1200 ml kerosene and 600 ml monoethyleneglycol. The kerosene phase running off was free from dihexyldiphosphoric acid ester.

EXAMPLE 8

(Invention)

The procedure was as in Example 6. The feed material was a phosphoric acid nonylester-mixture (41.8 weight % monononylphosphoric acid ester, 48.9% dinonylphosphoric acid ester and 7.9 weight % dinonyldiphosphoric acid ester) which was hydrolyzed for 3 hours at 80° C. with 1.5 weight % water and then introduced at a rate of 500 ml/h into the mixer in stage 3 of a mixer/settler unit comprising 5 stages. The quantities of kerosene and glycol conveyed per hour were 800 ml and 1000 ml, respectively. The separation in the two phases was good.

EXAMPLE 9

(Invention)

The procedure was as in Example 6, save that n-hexane was substituted for kerosene. 500 ml/h phosphoric acid ester mixture was used. After the extraction was terminated, the two phases were worked up distillatively. Hexane was distilled off from the hexane phase at 20° C. under a pressure of 100 mm of mercury. Di-(2-ethylhexyl)phosphoric acid ester with a purity of more than 95% remained behind. Glycol was distilled off from the glycol phase at 62° C. under a pressure of 2 mm mercury. Mono-(2-ethylhexyl)-phosphoric acid ester with a purity of 95% (determined in each case by P-NMR and titration) remained behind.

We claim:

1. A process for separating a mixture containing phosphoric acid monoalkylesters, phosphoric acid dialkylesters and minor proportions of diphosphoric acid dialkylesters, each with 6 to 12 carbon atoms in the alkyl radical, by extractively distributing them between an aliphatic or aromatic hydrocarbon as an unpolar solvent and a polar solvent, which comprises:

(a) admixing the ester mixture with the quantity of water stoichiometrically necessary for hydrolyzing the P-O-P-bond of the diphosphoric acid dialkylester with the resultant formation of the phosphoric acid monoalkylester, allowing the whole to remain for at least 1 hour at temperatures higher than 60° C., and (b) treating the partially hydrolyzed ester mixture in a countercurrent apparatus comprising n-stages with the solvents, which are immiscible or partially miscible with one another, so as to ensure introduction of pure solvent into stage 1 and stage n, respectively, and the introduction of partially hydrolyzed mixture into one of the stages 2 to $(n-1)$, n standing for a whole number of at least 3.

2. A process as claimed in claim 1, wherein a temperature of 80° to 100° C. is used in partial step (a) and the hydrolysis is effected over a period of 2 to 4 hours.

3. A process as claimed in claim 1, wherein n stands for a whole number of 3 up to 50.

4. A process as claimed in claim 1, wherein the untreated ester mixture contains 30 to 60 weight % each of phosphoric acid mono- and dialkylesters and 2 to 15 weight % of diphosphoric acid dialkylester.

5. A process as claimed in claim 1, wherein 1 to 3 parts by weight polar solvent and 1 to 3 parts by weight unpolar solvent are used per part by weight partially hydrolyzed ester mixture.

6. A process as claimed in claim 1, wherein the partially hydrolyzed ester mixture is metered into stage $n/2$ or, in the event of n standing for an uneven number, into stage $n/2+\frac{1}{2}$.

7. A process as claimed in claim 1, wherein the polar solvent is metered into stage 1, unpolar solvent is metered into stage n, and partially hydrolyzed ester mixture is introduced into a stage lying therebetween at a level which is the higher the higher the number of carbon atoms in the alkyl radical and the higher the quantitative ratio of phosphoric acid monoalkylester to phosphoric acid dialkylester in the partially hydrolyzed ester mixture.

8. A process as claimed in claim 1, wherein the counter-current apparatus is a mixer/settler-unit.

9. A process as claimed in claim 1, wherein the counter-current apparatus is a liquid/liquid extraction column provided with stationary or movable insert elements.

* * * * *